United States Patent [19]
Allen et al.

[11] Patent Number: 5,589,399
[45] Date of Patent: Dec. 31, 1996

[54] SYSTEM AND METHOD FOR PLASMA SEPARATION AND MEASUREMENT

[75] Inventors: Michael P. Allen, Los Altos; Robert F. Zuk, Burlingame; Lawrence M. Ensler, Los Altos, all of Calif.

[73] Assignee: First Medical, Inc., Mountain View, Calif.

[21] Appl. No.: 326,974

[22] Filed: Oct. 21, 1994

[51] Int. Cl.$^6$ .................................................. G01N 21/01
[52] U.S. Cl. .................... 436/169; 436/177; 436/178; 436/63; 422/58; 422/101; 435/2; 210/761; 210/500.21; 210/645
[58] Field of Search ..................... 210/645, 651, 210/500.36, 500.21, 506, 767; 436/169, 170, 177, 178; 422/63, 56–58, 66–67, 101, 100; 435/805, 2, 11, 288, 289, 291, 808, 25, 28, 19, 15, 14, 18.2, 287

[56] References Cited

U.S. PATENT DOCUMENTS

| | | | |
|---|---|---|---|
| 3,663,374 | 5/1972 | Moyer et al. | 195/103.5 |
| 4,477,575 | 10/1984 | Vogel et al. | 436/170 |
| 4,678,757 | 7/1987 | Rapkin et al. | 436/169 |
| 4,753,776 | 6/1988 | Hillman et al. | 422/101 |
| 4,816,224 | 3/1989 | Vogel et al. | 422/55 |
| 4,933,092 | 6/1990 | Aunet et al. | 210/729 |
| 4,952,516 | 8/1990 | Matkovich | 436/170 |
| 4,987,085 | 1/1991 | Allen et al. | 436/169 |
| 4,999,163 | 3/1991 | Lennon et al. | 422/58 |
| 5,000,922 | 3/1991 | Turpen | 422/101 |
| 5,110,724 | 5/1992 | Hewett | 435/11 |
| 5,132,086 | 7/1992 | Allen et al. | 422/56 |
| 5,135,719 | 8/1992 | Hillman et al. | 422/101 |
| 5,147,606 | 9/1992 | Charlton et al. | 422/56 |
| 5,186,843 | 2/1993 | Baumgardner et al. | 210/767 |
| 5,238,652 | 8/1993 | Sun et al. | 436/63 |
| 5,262,067 | 11/1993 | Wilk et al. | 210/767 |
| 5,266,219 | 11/1993 | Pall et al. | 210/767 |
| 5,308,483 | 5/1994 | Sklar et al. | 210/232 |

*Primary Examiner*—James C. Housel
*Assistant Examiner*—Rachel Freed
*Attorney, Agent, or Firm*—Townsend and Townsend and Crew LLP

[57] ABSTRACT

The system for transferring plasma to a test substrate comprises an applicator and the test substrate. The applicator includes a blood reservoir and a filter element which separates cellular components from the blood as plasma is passed to the test substrate. The test substrate includes an absorptive element which receives the plasma from the applicator. In one embodiment, measured amounts of plasma are transferred when the absorptive element becomes saturated, thus stopping the flow of plasma. In another embodiment, excess blood and cellular components are removed from the measured plasma by disengaging the applicator from the test substrate. In another embodiment, plasma transferred to the absorptive element is eluted from the absorptive element by subsequent application of an elution medium.

19 Claims, 7 Drawing Sheets

FIG_1

FIG_3

FIG_2

FIG_4A

FIG_4B

FIG_4C

FIG_4D

FIG_4E

FIG_4F

FIG_4G

SYSTEM AND METHOD FOR PLASMA SEPARATION AND MEASUREMENT

BACKGROUND OF THE INVENTION

1. Field of the Invention

The present invention relates generally to systems and methods for assaying biological samples. Particularly, the present invention relates to a system and method for separating plasma from whole blood and transferring measured amounts of the plasma to a test substrate.

Many diagnostic markers and other analytes are best determined from patient blood samples. The ability to measure such markers and analytes directly in blood, however, is problematic because of the presence of blood cells, particularly red blood cells, in whole blood. Thus, a majority of analytical systems and methods intended for measuring blood markers and analytes rely on detection in a plasma or serum sample, not in a whole blood sample.

A wide variety of blood separation systems and methods have been developed over the years particularly for use in performing plasma and serum assays. Such systems may be generally categorized as centrifugal, chemical, and filtration. Centrifugal systems rely on centrifugation to remove cellular components from the blood. Chemical systems rely on antibodies, lectins, or the like, for binding and removing cellular components. Finally, filtration relies on chromatographic and/or size-exclusion filtration elements for separating the cellular blood components from the resulting plasma fraction.

The present invention is concerned in particular with filtration systems and methods for producing plasma from whole blood prior to performing an assay on the plasma. Heretofore, filtration elements have often been constructed integrally in assay devices, where blood is applied to the filter element and plasma is separated and flows to a reaction zone, usually without precise measurement of the plasma and without the ability to separate the excess blood and cellular blood components from the assay device. Such prior assay devices were often limited in their ability to provide diluents, eluents, and other liquid reagents in the measurement system. Furthermore, such prior devices were frequently limited to a single reaction zone for determining a single marker or analyte.

For these reasons, it would be desirable to provide improved systems and methods for separating plasma from whole blood for use in assays and assay devices. It would be particularly desirable if such systems and methods could provide for accurate and precise (receptacle) measurement of the plasma being separated as well as for direct transfer of the measured plasma volume to a test substrate. It would be further desirable if systems and methods allowed for complete separation of the excess blood and cellular components from the separation device, as well as for subsequent elution of the separated plasma to one or more associated reaction zones. In particular, it would be desirable if the systems and methods of the present invention provided for assays employing a plurality of reaction zones capable of measuring a multiplicity of analytes from a single blood sample, particularly from a low volume blood sample of 500 µl or below.

2. Description of the Background Art

Filter elements for separating plasma from whole blood in combination with absorptive pads are shown in a number of patents, including U.S. Pat. Nos. 5,262,067; 5,132,086; 5,110,724; 4,987,085; 4,933,092; 4,816,224; 4,753,776; 4,477,575; and 3,663,374. In particular, U.S. Pat. No. 5,132,086 shows a device where sample is absorbed into a filtering pad, optionally by dipping the pad into the sample to obtain a semiquantitative volume of sample, and sample then allowed to flow through a reaction zone on an adjacent absorptive strip. U.S. Pat. No. 5,110,724 shows a device for separating plasma from whole blood and distributing the plasma over an absorptive distribution strip. The plasma is then transferred to a plurality of separate reaction pads by simultaneously contacting the pads with the distribution strip. U.S. Pat. No. 4,987,085 shows a device having a cell-filtering structure formed over an absorptive pad. Blood is applied to the filtering structure, and the filtering structure removed after plasma has been absorbed in the pad. U.S. Pat. Nos. 4,816,224 and 4,477,575 describe a device having a cell-filtering structure removably formed over an absorptive reaction layer. Other patents showing assay devices including separation membranes and absorptive pads include U.S. Pat. Nos. 4,678,757; 4,952,516; 4,999,163; 5,000,922; 5,135,719; 5,186,843; 5,266,219; and 5,308,483.

SUMMARY OF THE INVENTION

According to the present invention, systems and methods are provided for separating plasma from whole blood and simultaneously transferring measured amounts of the separated plasma to a test substrate. The systems and methods are capable of delivering very precise and accurate plasma volumes to the test substrate, typically within 15% and preferably within 5% of the nominal value, even from very small whole blood samples, typically below 500 µl and often below 50 µl. The separated cellular components and excess whole blood may be completely removed from the test substrate, and an eluent subsequently applied to the test substrate to distribute the plasma to an associated reaction zone, usually on the test substrate. Frequently, a plurality of reaction zones will be located on the test substrate, permitting simultaneous detection of a multiplicity of analytes. The ability to initially provide such accurate and precise plasma volumes, as well as to subsequently elute the measured plasma to associated reaction zone(s), permits accurate quantitative measurement of target markers and analytes even when the initial blood sample is very small and the separated plasma is highly diluted.

A system according to the present invention for transferring measured amounts of plasma from unmeasured whole blood samples to a test substrate comprises an applicator and a plasma-receiving test substrate. The applicator includes a blood-receiving reservoir which is in fluid communication with a plasma transfer port. A filter member extends across the plasma transfer port, where the filter member permits the passage of plasma and plasma macromolecules but inhibits the passage of blood cells. Thus, plasma is separated from the blood in the reservoir as the plasma advances through the filter member under capillary forces, as described in more detail below.

The plasma-receiving test substrate includes an absorptive element having a contact surface configured to engage the plasma transfer port of the applicator. The absorptive element, which may be a fiber capillary matrix or a molded capillary matrix, will usually have a plasma capacity which is less than the plasma capacity of the blood reservoir in the applicator. Thus, plasma transfer from the applicator will terminate as soon as the plasma has saturated the absorptive element, resulting in the transfer of a very precise and accurate volume of plasma to the test substrate. Usually, the applicator will be removed from the test substrate leaving the transferred plasma volume available for subsequent testing, free from cellular components and excess blood.

In a preferred aspect of the system of the present invention, the applicator further includes a tube for drawing blood into the blood-receiving reservoir. Optionally, the tube may be a capillary tube or needle suitable for pricking a patient's finger to draw a small blood volume e.g. hypotube. Alternatively, the tube may be a needle suitable for penetration through the plenum or stopper of a blood collection vessel in which patient blood has previously been collected, e.g. a vacuum blood collection device. Usually, the blood-receiving reservoir will have a volume in the range from 50 µl to 500 µl, and the plasma transfer port will have an area in the range from 15 mm² to 200 mm². The filter member in the applicator will also preferably have a crowned cross-sectional profile to enhance contact with the contact surface of the absorptive element on the plasma-receiving test substrate.

In a further preferred aspect of the system of the present invention, the absorptive element on the test substrate will have a contact area in the range from 10 mm² to 200 mm² and a plasma capacity below 200 µl, preferably in the range from 1 µl to 100 µl. The plasma-receiving test substrate optionally further includes a fluid-receiving surface disposed adjacent to the absorptive element so that plasma eluted from the absorptive element will be received on the surface. The plasma-receiving test substrate may further include at least one reaction zone disposed on the fluid-receiving surface to permit reaction of the eluted plasma for the detection of a target marker, analyte, or the like. Preferably, the test substrate will include a plurality of reaction zones, optionally arranged on a disk having the absorptive element at its center.

A first method for transferring plasma from unmeasured blood samples to a test substrate comprises applying a volume of whole blood to an absorptive element through a filter membrane. The filter membrane permits the passage of plasma and plasma macromolecules but inhibits the passage of blood cells so that blood cells are retained above the filter membrane. An elution medium is subsequently applied to the absorptive element to elute the separated plasma to a reaction zone on the test substrate. Usually, the absorptive element will have a plasma capacity which is less than the amount of plasma in the whole blood volume, thus assuring that a precisely measured volume of plasma is transferred to the test substrate. By then removing the filter member, plasma can be eluted from the absorptive element without interference from the separated cellular components and excess whole blood.

According to a second method of the present invention, metered amounts of plasma are transferred from unmeasured blood samples to a test substrate by applying a volume of whole blood to an absorptive element through a filter member. The absorptive element has a plasma capacity which is less than the amount of plasma in the whole blood volume so that the absorptive element becomes saturated with a predetermined amount of plasma. The filter member permits the passage of plasma and plasma macromolecules but inhibits the passage of blood cells, and excess blood and blood cells are thus retained on the filter membrane. By removing the filter member from the absorptive element, excess blood and blood cells are separated from the precisely measured amount of plasma absorbed in the absorptive element. Optionally, an elution medium may be applied to the absorptive element after the filter membrane has been removed so that plasma absorbed in the absorptive element is eluted to a reaction zone on a fluid-receiving surface of the test substrate.

According to a third method of the present invention, measured amount of plasma are transferred from unmeasured blood samples to a test substrate by applying a volume of whole blood to an absorptive element through a filter membrane. The filter membrane permits the passage of plasma and plasma macromolecules, but inhibits the passage of blood cells so that blood cells are retained on the filter member. The filter member is removed from the absorptive element after a time selected to permit the transfer of a preselected amount of plasma to be absorbed in the absorptive element. Usually, the filter member is removed before the absorptive element becomes saturated with plasma. Optionally, an elution medium is applied to the absorptive element after the filter member has been removed so the plasma absorbed in the absorptive element is eluted to a reaction zone on a fluid-receiving surface of the test substrate.

According to a fourth method of the present invention, measured amounts of plasma are transferred from whole blood to a test substrate by first drawing blood through a capillary tube into a reservoir in an applicator. A filter membrane extending across a transfer port in the applicator is then contacted against an absorptive element on the test substrate, where the absorptive element has a plasma capacity which is less than the amount of plasma in the blood reservoir. The filter member permits the passage of plasma and plasma macromolecules but inhibits the passage of blood cells so that excess blood and blood cells are retained on the filter member. The filter member is removed from the absorptive element after the absorptive element has become saturated with a predetermined amount of plasma.

According to the fifth method of the present invention, measured amounts of plasma are transferred from whole blood to a test substrate by first drawing blood through a needle inserted into a collection device filled with patient blood, e.g. a vacuum blood collection device, into a reservoir in an applicator. A filter membrane extending across a transfer port in the applicator is then contacted against an absorptive element on the test substrate, where the absorptive element has a plasma capacity which is less than the amount of plasma in the blood reservoir. The filter member permits the passage of plasma and plasma macromolecules but inhibits the passage of blood cells so that excess blood and blood cells are retained on the filter member. The filter member is removed from the absorptive element after the absorptive element has become saturated with a predetermined amount of plasma.

DESCRIPTION OF THE SPECIFIC EMBODIMENTS

The present invention includes a system and method for providing plasma, usually in precisely measured volumes, for subsequent analysis for the determination of target markers, analytes, enzyme activities, proteins, small molecules, infectious organisms, drugs, and the like. Plasma consists of whole blood from which the blood cells, including both red blood cells and white blood cells, have been separated. Generally, blood proteins and other macromolecules, including the clotting proteins, immunoglobullins, and other blood factors and non-cellular components, remain in the plasma. In particular, the present invention provides for filtration of cellular components from whole blood to provide plasma as will be described in more detail hereinbelow. All blood components substantially smaller than the cellular components will remain in the separated plasma. Thus, virtually any test which can be performed on plasma can utilize plasma obtained by the systems and methods described below.

Separation of cellular components from whole blood according to the present invention will generally be obtained by two-stage filtration with a chromatographic filter element in series with a size-exclusion filter element. The chromatographic filter element will typically be a depth filter, often including two or more separate layers. The chromatographic filter element performs an initial separation of cellular components from the plasma based on chromatographic principles, i.e. the plasma will travel through the chromatographic element at a rate faster than the blood cells which, because of their size are preferentially slowed. The chromatographic filter element can be composed of any conventional filter medium, such as glass fiber, polyester fiber, plastic fiber, metal fiber, composite cellulose and synthetic fiber, nylon mesh, polyester mesh, synthetic fabric, and the like. A preferred chromatographic filter element material is glass fiber. The area and depth of the chromatographic filter element will depend on the volume of plasma to be separated from the applied whole blood, as described in more detail below. Typically, the volume of the chromatographic filter element will be in the range from 25 mm$^3$, preferably from 25 mm$^3$ to 700 mm$^3$. The depth of the chromatographic filter element will typically be in the range from 1 mm to 10 mm, usually from 2 mm to 6 mm.

The size-exclusion filter membrane will have a pore size selected to exclude the passage of cells, typically being less than 7 µm, preferably being in the range from 0.1 µm to 7 µm, more preferably being from 0.4 µm to 3 µm. The size-exclusive membrane can be composed of any conventional membrane material, such as nitrocellulose, cellulose acetate, regenerated cellulose, polycarbonate, polyamide, and the like. A preferred size-exclusion filter membrane is polycarbonate.

The chromatographic filter element will have a volume which is sufficiently large to retain blood cells and prevent blockage of the size-exclusion membrane so that a desired volume of plasma can pass through the combined filter member. Usually, the plasma capacity of the filter member will be larger than that of the absorptive element on the test substrate, as described in detail below in connection with certain embodiments of the test system. In some cases, however, such as when plasma measurement is not being performed or plasma measurement is being performed by timed plasma transfer techniques, the plasma capacity of the filter member could be smaller than the plasma capacity of the absorptive element.

Materials and constructions for two-stage filter systems suitable for use in the present invention are described in U.S. Pat. No. 3,663,374, the full disclosure of which is incorporated herein by reference.

Plasma passing through the filter member is transferred to an absorptive element on a plasma-receiving substrate. The absorptive element can be any material or structure which is capable of absorbing the plasma by capillary action. In a first exemplary embodiment, the absorptive element will be composed of a fiber capillary matrix, such as cellulose paper, cellulose acetate, nitrocellulose, regenerated cellulose, polyamide, hydrophilic-treated polyethylene, nylon mesh, hydrophilic-treated polyester mesh, and the like. Indeed, virtually any liquid-absorptive material which can absorb the plasma without deleterious interaction with the components to be measured might find use.

Alternatively, the absorptive element can be defined by a molded capillary matrix, such as those illustrated in FIGS. 4A–4G and described in more detail hereinafter. Such molded structures provide for a very precise capillary volume to enhance the accuracy and repeatability of plasma measurement performed by the present invention.

The absorptive element of the present invention will frequently be free of any reactive components which would react or otherwise interact with the target markers, analytes, or other components in the plasma being transferred. In such cases, analysis of the plasma will be performed by eluting or otherwise removing the plasma to an adjacent reaction zone as described hereinafter. Alternatively, analysis could be performed by subsequently applying test reagents directly to the absorptive element and reading the results on the element itself. The latter protocol, however, is generally less preferred since the absorptive element will usually be saturated with plasma, making it difficult to apply further test reagents.

The test substrate will frequently include other components or elements intended to provide or be part of the analysis to be performed. For example, the test substrate may comprise a fluid-receiving surface, where the absorptive element is located on said surface. Application of an elution medium to the absorptive element can then cause flow of the plasma (diluted with the elution medium) onto the fluid-receiving surface. Analysis can then be performed by providing reaction zones on the fluid-receiving surface or by further transferring the separated plasma remotely located reaction zone(s). The reaction zones will frequently provide specific binding reagents capable of capturing a target analyte or marker in the plasma. Optionally, the elution medium may contain other components of a test system in order to perform a desired analysis.

The applicator of the present invention includes a transfer port and a blood-receiving reservoir adjacent the filter member. The transfer port will have an area in the range from 15 mm$^2$ to 200 mm$^2$, preferably being from 25 mm$^2$ to 100 mm$^2$, and usually although not necessarily having a circular periphery. The volume of the reservoir will typically be in the range from 50 µl to 500 µl, preferably from 100 µl to 400 µl. The volume includes the blood and plasma capacity of the filter member. That is, the applicator will have a total blood and plasma capacity which is the total of that present in the filter member (prior to transfer to the plasma-receiving test substrate) and that present in the "empty" volume of the reservoir (i.e. the volume which is not occupied by filter element). As plasma is drawn from the filter element to the absorptive element on the test substrate, it will be appreciated that blood in the empty volume of the reservoir will pass into the filter element, where plasma is separated by the filter element components as described above. The total amount of plasma available to be transferred to the absorptive element, however, will be the total of that initially present both in the filter element and the empty volume of the reservoir.

Figure 1:
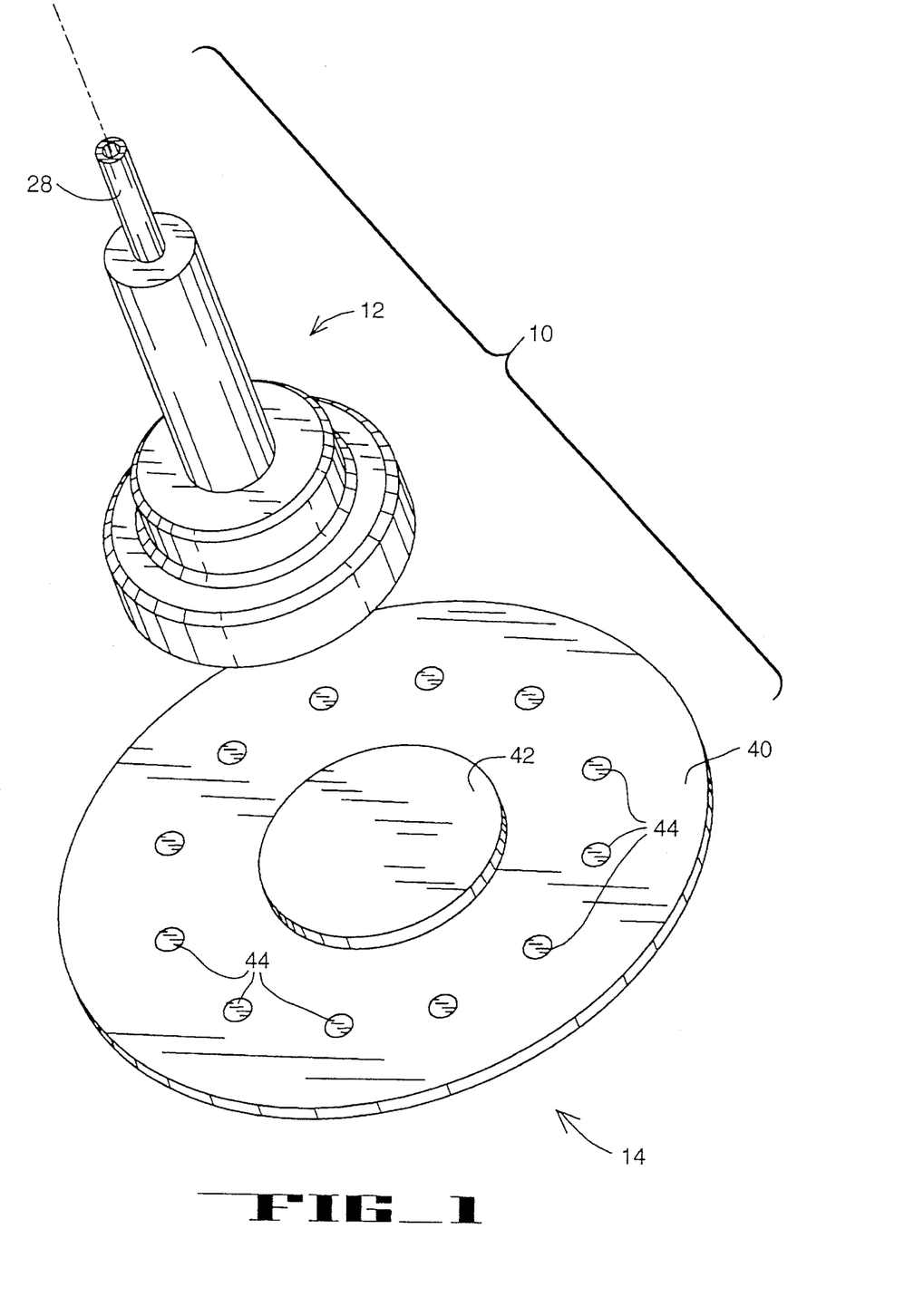
FIG. 1 is a perspective view of a test system comprising an applicator and a test substrate constructed in accordance with the principles of the present invention.
Figure 2:
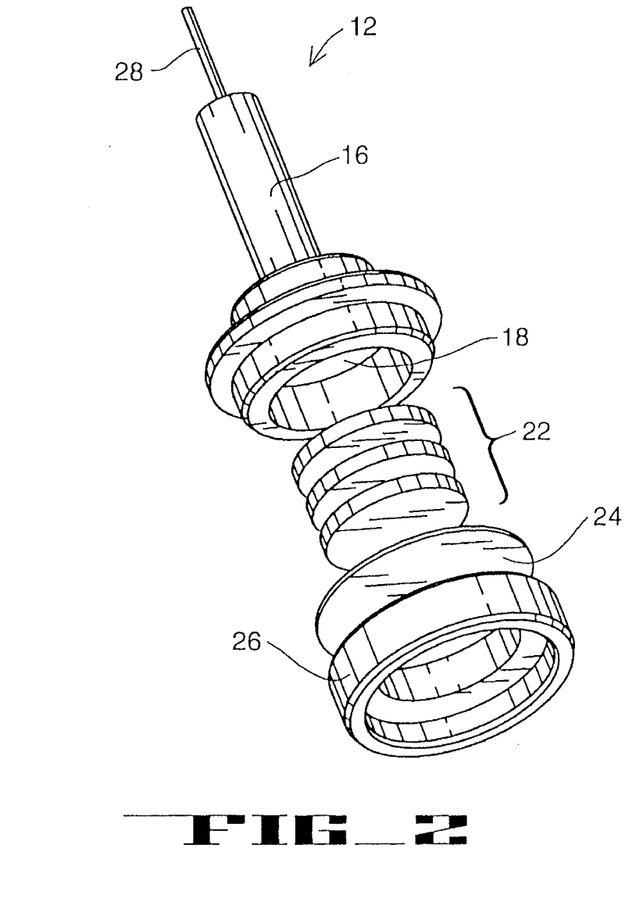
FIG. 2 is an exploded view of the applicator of the system of FIG. 1.
Figure 3:
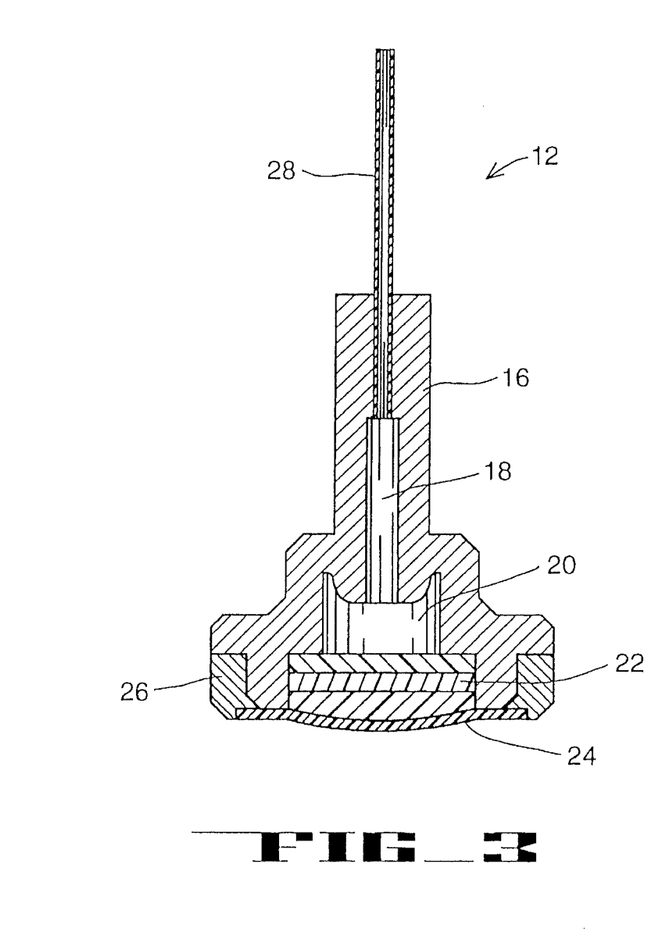
FIG. 3 is a cross-sectional view of the applicator of the system of FIG. 1.

Referring now to FIGS. 1–3, a test system 10 comprises an applicator 12 and a test substrate 14. The applicator 12 includes a casing 16 which is typically formed from molded plastic, such as polystyrene. Casing 16 has an axial blood passage 18, an open blood reservoir 20, and a three-layer filter element 22 (FIG. 3). The filter element 22 typically comprises three layers of glass fiber. Filter membrane 24 defines a lower contact surface for the applicator, as described in more detail hereinafter. The assembly is held together by ring 26, and a capillary tube 28, typically a hypotube suitable for obtaining a blood sample by finger prick, is mounted next to the axial blood passage 18.

The test substrate 14 is illustrated as a disc 40 having absorptive element 42 at its center and a plurality of reaction zones 44 spaced radially outward from the absorptive element. The absorptive element 42 is shown as a fiber matrix, such as a cellulose acetate disk. The reaction zones 44 may conveniently be a specific binding substance, such as an antibody, biotin, avidin, ligand, receptor, or the like. The disk 40 may be composed of a variety of materials, such as acrylic or optical quality polystyrene. The coupling of specific binding proteins and other substances to such solid phase materials is well described in the scientific and patent literature.

The reaction zone 44 will contain diffusively or non-diffusively bound reagent(s) that can react directly or indirectly with the sample analyte or a specific reaction product of the sample analyte. The reaction zone can thus contain any assay reagent(s), including but not limited to, one member of a binding pair such as an antibody, lectin, avidin, strepavidin or biotin, or may include components of a signal producing system or a combination of reagents to carry out assay methods. The reaction zone will ultimately produce or cause to produce a specific signal in response to a sample analyte. The signal is proportional directly or inversely to the sample analyte concentration.

The disk 40 will be particularly suitable for use in interferometric assays, such as those described in co-pending PCT Application US94/07184, (which designates the U.S.) the full disclosure of which is incorporated herein by reference.

Figure 4A:
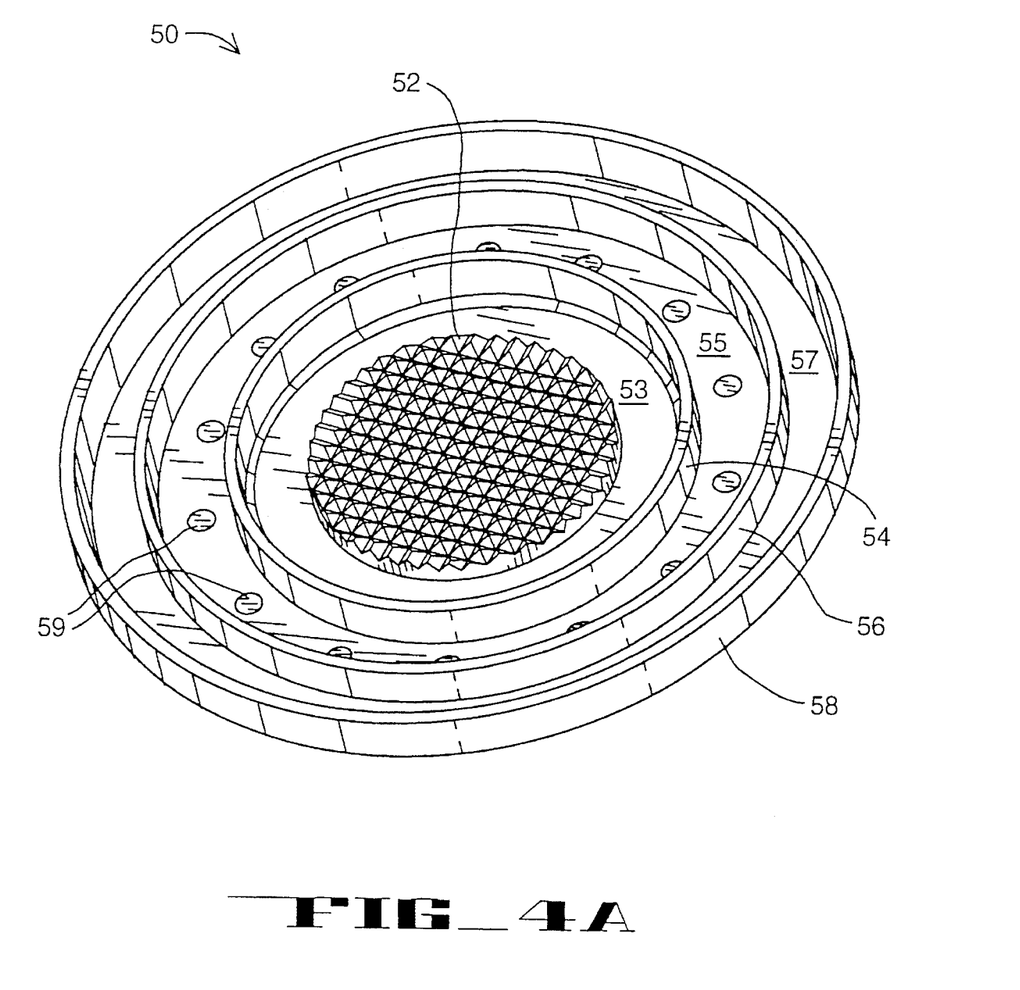
FIGS. 4A–4G illustrates alternative embodiments of the test substrate and plasma absorptive element of the system of FIG. 1.
Figure 4B:
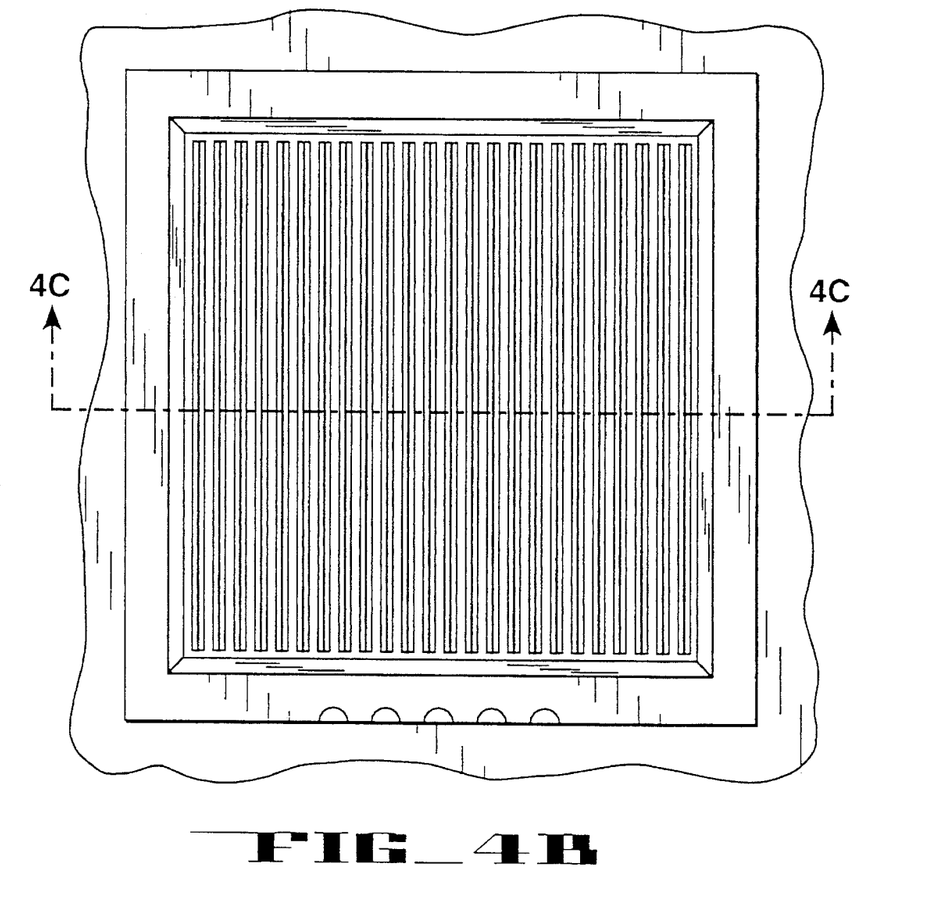
Figure 4C:
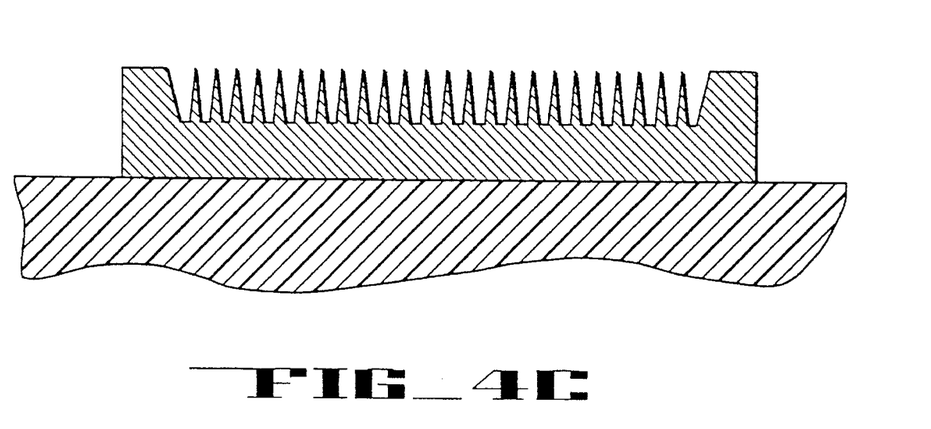
Figure 4D:
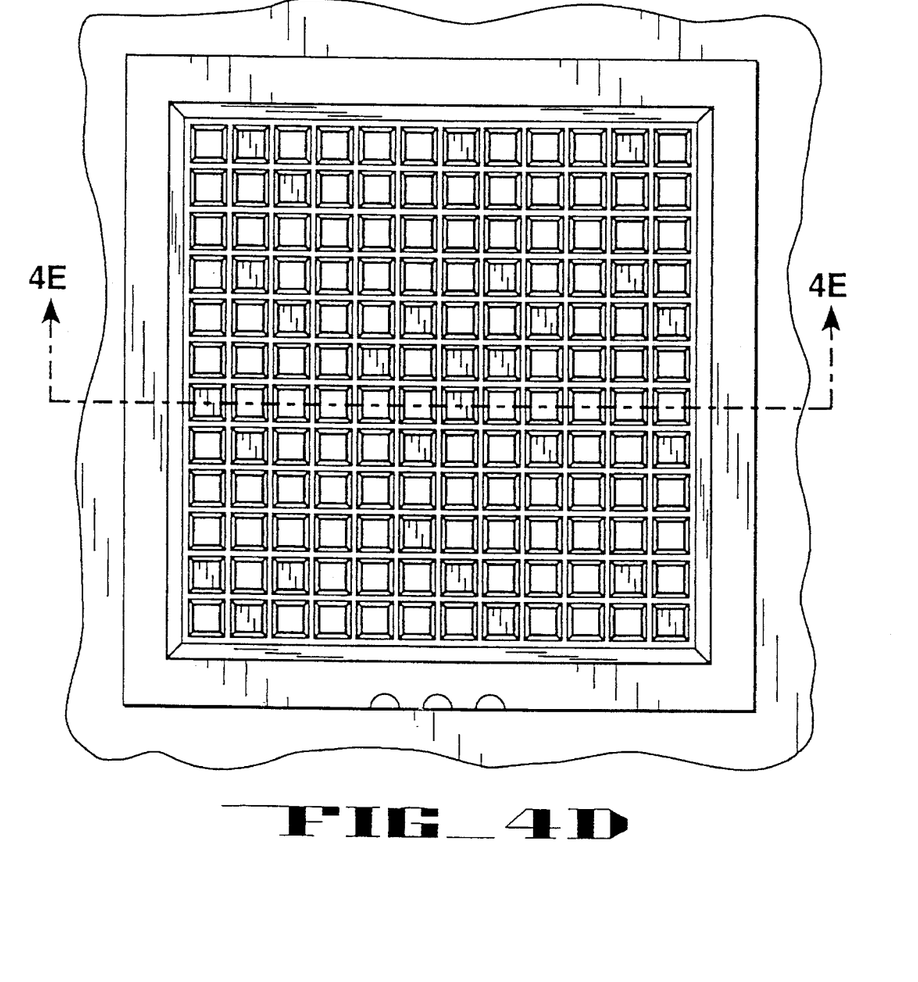
Figure 4E:
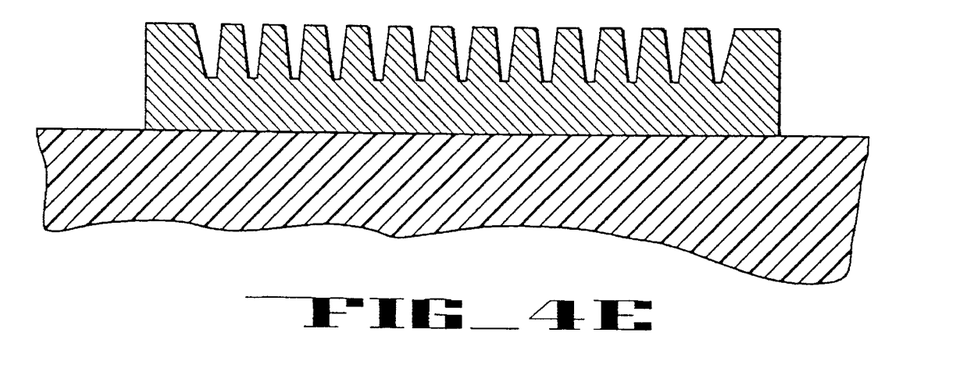

A test substrate 50 having an alternative construction is illustrated in FIG. 4A. Test substrate 50 is a disk having a molded capillary matrix 52 disposed at its center. The molded capillary element 52 comprises an array of molded pyramidal protrusions formed over a generally flat plane. The interstices between the protrusions have capillary dimensions which are able to absorb a precise volume of plasma from the applicator 12 of the system of FIG. 1. Test substrate 50 further includes a plurality of concentric walls 54, 56, and 58. These walls define plurality of annular regions. Region 53 defined wall 54 is the plasma elution and mixing region. After a measured volume of plasma is transferred to the capillary element 52, the plasma is washed into region 53. Additional reagent(s) may be added to the region 53 and mixed with the plasma. The plasma and optional reagent(s) are then transferred to a reaction region 55 defined by concentric wall 56. Region 55 will include a plurality of spaced-apart reaction zones 59 similar to zones 44 described with reference to FIG. 1. After the reaction is complete, the plasma may be transferred to a waste collection region 57 defined by wall 58.

Figure 4F:
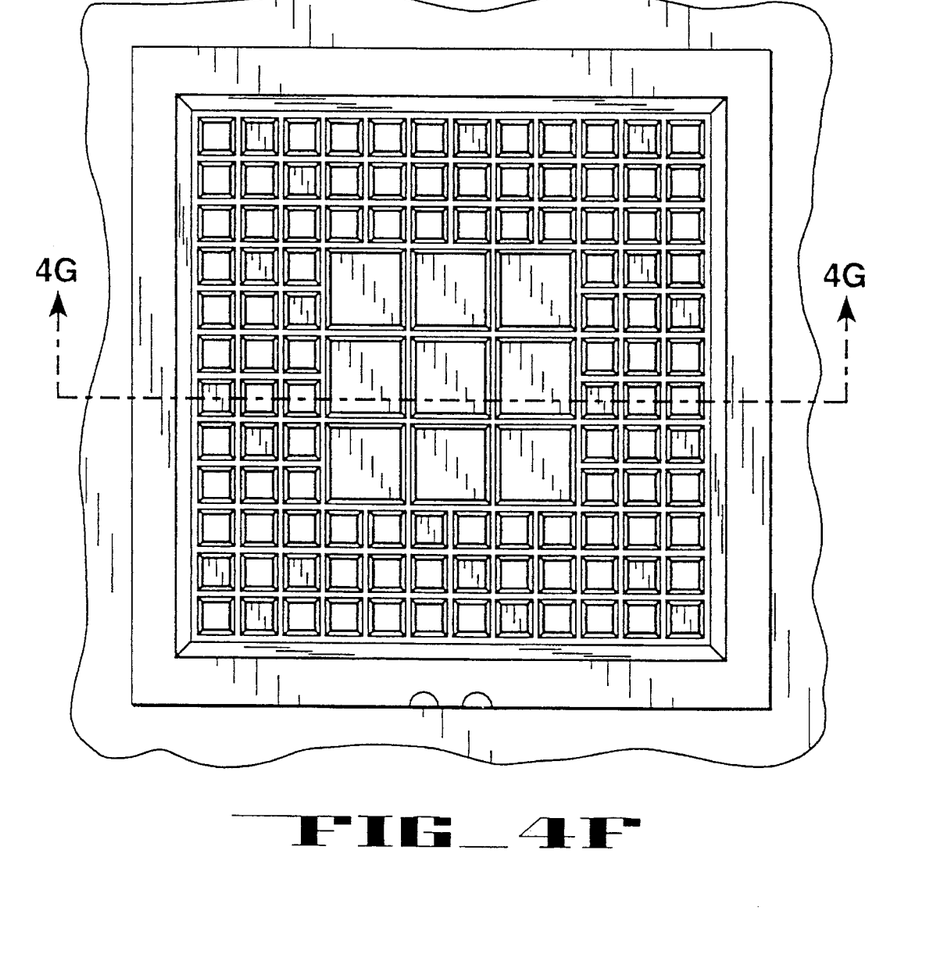
Figure 4G:
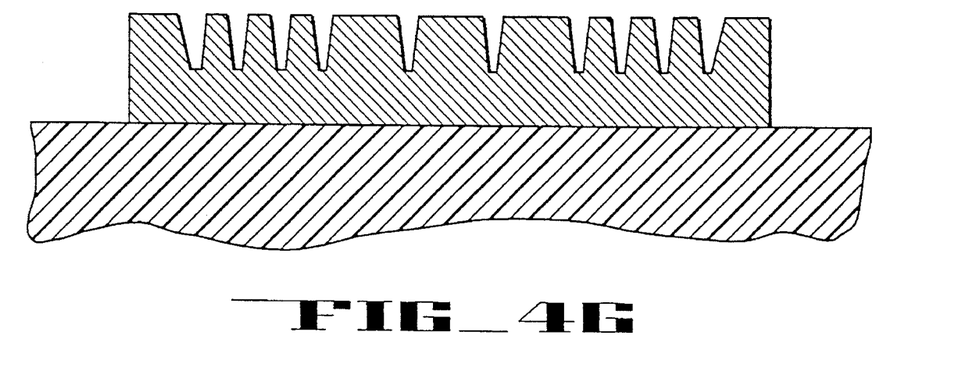

Alternative capillary structures which could be employed on the test substrate 40 or 50 are illustrated in FIGS. 4B–4G. Such capillary structures include a parallel capillary grating (FIGS. 4B and 4C), a uniform checkerboard pattern capillary grating (FIGS. 4D and 4E), and a checkerboard pattern capillary grating having a central area with a reduced capillary density (FIGS. 4F and 4G). The reduced capillary density area of the capillary structure of FIGS. 4F and 4G will be sized and configured to engage the plasma transfer port of the applicator. The area of reduced capillary density permits withdrawal of the application from the capillary structure without substantial loss of transferred fluid sample. Surface tension and liquid cohesion within the filter matrix of the applicator can cause fluid sample to be partially withdrawn from the capillary grating as the applicator is disengaged. Reducing the density of the capillary grating in the region of the direct contact with the filter reduces direct fluid-to-fluid contact and decreases the loss of precision associated with such sample fluid loss.

Figure 5A:
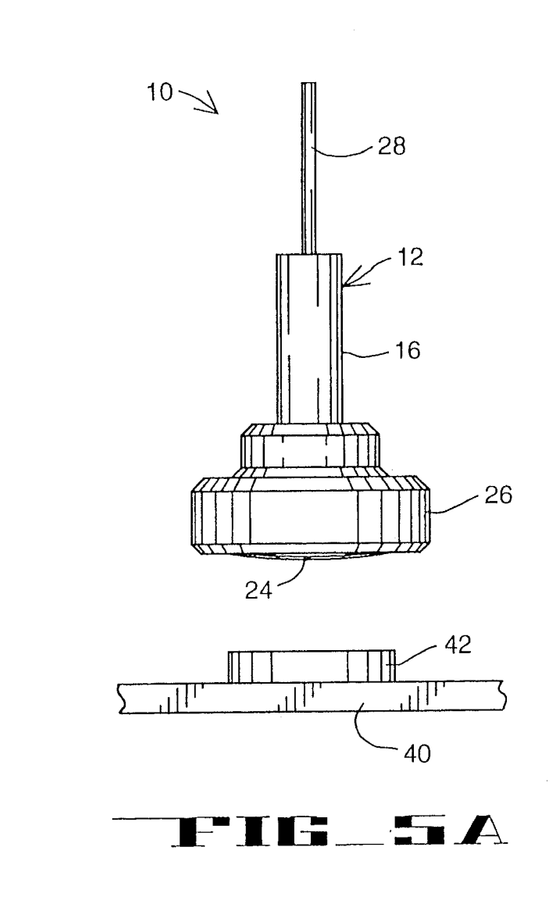
FIGS. 5A–5C illustrate use of the system of FIG. 1 in transferring a measured amount of plasma to the test substrate and subsequently eluting the plasma from absorptive element on the substrate to an adjacent fluid-receiving surface.
Figure 5B:
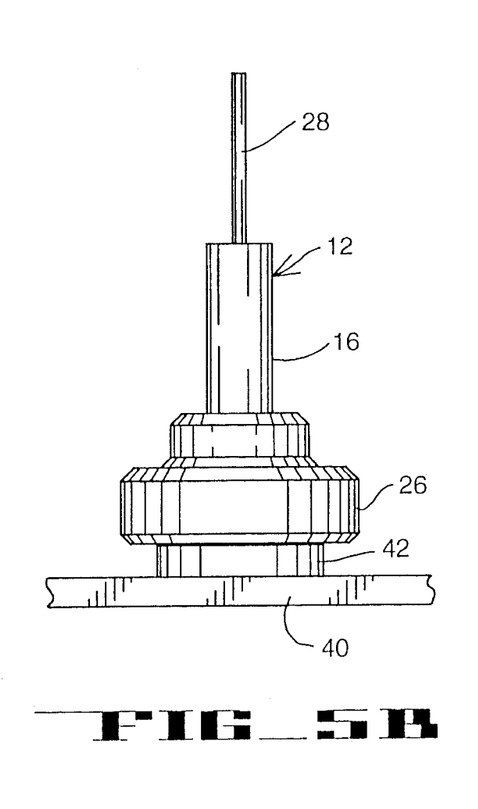
Figure 5C:
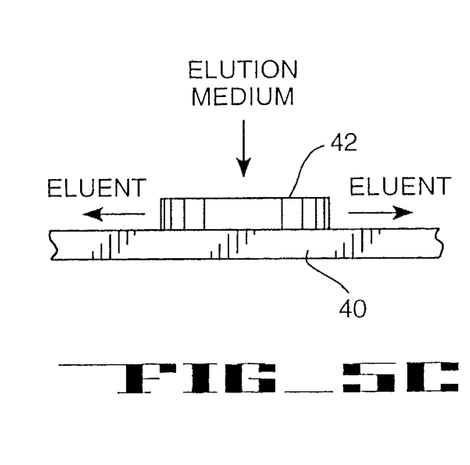

Referring now to FIGS. 5A–5C, use of the applicator 12 in transferring a plasma sample to an absorptive element 42 on test substrate 40 will be described. The applicator 12 is filled with blood, typically by finger prick with the capillary tube 28 (FIG. 5A). After the blood has been obtained, applicator 12 is pressed against absorptive element 42 of test substrate 40 by engaging the crowned filter membrane 24 against an upper, plasma-receiving surface of the element 42. The applicator will be pressed against the absorptive element 42 (as illustrated in FIG. 5B) until the desired volume of plasma has been transferred. In a preferred embodiment, the contact will be maintained until the absorbed development 42 is saturated with plasma, and the applicator 12 can be removed from the test substrate at any time after saturation has been achieved. In an alternative embodiment, the absorptive element 42 will have a plasma capacity which may be greater than that of the plasma carried in the applicator 12. In that case, the applicator 12 will be removed after a time which is selected to permit transfer of a fixed amount of plasma to the absorptive element 42. Generally, such time transfers will be less desirable since they will be less accurate. In both cases, the crowned profile of the filter membrane 24 is advantageous since it helps assume continuous contact between the membrane and the absorptive element 42 as the filter element 22 is compressed. Alternatively, or additionally, the contact surface of the absorptive element 42 could also be crowned to promote good contact with the filter membrane 24.

After the applicator 12 is removed, as shown in FIG. 5C, an elution medium may be applied to the absorptive element 42, resulting in the outward flow of eluant from the element 42 to the plasma-receiving surface of the substrate 40. As shown in FIG. 1, reaction zones will typically be present on the substrate 40, allowing reaction with the eluant to perform a desired assay or test. Alternatively, the plasma could be removed from the absorptive element 42 (or a capillary equivalent as illustrated in FIGS. 4A–4G) by centrifugation, i.e. spinning the substrate sufficiently rapidly to cause the plasma to flow radially outward from the absorptive element due to centrifugal forces. Additional reagents may be added as necessary to perform the desired assay or test.

Although the foregoing invention has been described in some detail by way of illustration and example, for purposes of clarity of understanding, it will be obvious that certain changes and modifications may be practiced within the scope of the appended claims.

What is claimed is:

1. A system for transferring measured amounts of plasma from unmeasured blood samples to a test substrate, said system comprising:

an applicator having a blood-receiving reservoir with a predetermined plasma capacity and a single plasma transfer port having a cross-sectional area and shape in fluid communication with the reservoir and including a filter member extending across the plasma transfer port, wherein the filter member permits the passage of plasma and plasma macromolecules but inhibits the passage of blood cells;

a plasma-receiving test substrate having a surface; and at least one reaction zone on the substrate surface; and a single absorptive element on the substrate surface having a contact surface with a shape and area substantially identical to those of the port so that the contact surface is configured to engage the plasma transfer port and a plasma capacity which is less than the plasma capacity of the reservoir, wherein plasma transferred from the reservoir will saturate the absorptive element to provide a measured amount of plasma on the substrate; and wherein the at least one reaction zone is spaced from said single absorptive element.

2. A system as in claim 1, wherein the applicator further includes a capillary tube for drawing blood into the blood-receiving reservoir.

3. A system as in claim 1, wherein the blood-receiving reservoir has a volume in the range from 50 µl to 500 µl.

4. A system as in claim 3, wherein the plasma transfer port has an area in the range from 15 mm$^2$ to 200 mm$^2$ and the filter member has a crowned profile to enhance contact with the contact surface of the absorptive element.

5. A system as in claim 1, wherein the filter member comprises a chromatographic filter element in series with a size-exclusion element, wherein the chromatographic filter element slows the flow of blood cells relative to that of plasma and the size-exclusion element permits plasma flow and blocks the passage of blood cells.

6. A system as in claim 5, wherein the chromatographic filter element has a volume which is sufficiently large to retain blood cells and inhibit blockage of the filter member in order to permit a volume of plasma flow through the filter member which is larger than the plasma capacity of the absorptive element.

7. A system as in claim 6, wherein the chromatographic filter element has a volume in the range from 25 mm$^3$ to 1000 mm$^3$ and is composed of a material selected from the group consisting of glass fiber, polyester fiber, plastic fiber, metal fiber, composite cellulose and synthetic fiber, nylon mesh, polyester mesh, and synthetic fabric.

8. A system as in claim 5, wherein the size-exclusion element comprises a microporous membrane having a pore size below 7 µm and composed of a material selected from the group consisting of nitrocellulose, cellulose acetate, regenerated cellulose, polycarbonate, and polyamide.

9. A system as in claim 1, wherein the absorptive element has contact area in the range from 10 mm$^2$ to 200 mm$^2$ and a plasma capacity below 200 µl.

10. A system as in claim 9, wherein the plasma capacity of the absorptive element is in the range from 1 µl to 100 µl.

11. A system as in claim 1, wherein the absorptive element comprises a fiber capillary matrix or a molded capillary matrix.

12. A system as in claim 11, wherein the fiber capillary matrix is composed of a material selected from the group consisting of cellulose paper, cellulose acetate, nitrocellulose, regenerated cellulose, polyamide, hydrophilic-treated polyethylene, nylon mesh, and hydrophilic-treated polyester mesh.

13. A system as in claim 1 wherein the test substrate is a disk having the absorptive element at the center of a circular fluid-receiving surface and a plurality of reaction zones spaced radially outward from the absorptive element.

14. A system for transferring measured amounts of plasma from unmeasured blood samples to a test substrate, said system comprising:

an applicator having a blood-receiving reservoir and a plasma transfer port in fluid communication with the reservoir and including a filter member extending across the plasma transfer port, wherein the filter member permits the passage of plasma and plasma macromolecules but inhibits the passage of blood cells, and wherein the plasma transfer port has a plasma port cross-sectional geometry; and a plasma-receiving test substrate having a surface, said surface having thereon at least one reaction zone, and an absorptive element having a contact surface configured to engage the plasma transfer port and a plasma capacity which is less than a plasma capacity of the reservoir, and at least one reaction zone separated from the absorptive element by a fluid-receiving surface, wherein plasma transferred from the reservoir will saturate the absorptive element to provide a measured amount of plasma on the substrate and wherein the at least one reaction zone is spaced from said single absorptive element.

15. A system as claimed in claim 14, wherein at least one reaction zone comprises a plurality of reaction zones, each reaction zone having a specific binding reagent.

16. A system as claimed in claim 1, wherein the absorptive element is free of any reactive components which would interact with target plasma components.

17. A system for transferring measured amounts of plasma from unmeasured blood samples to a test substrate, said system comprising:

an applicator having a blood-receiving reservoir and a plasma transfer port in fluid communication with the reservoir and including a filter member extending across the plasma transfer port, wherein the filter member permits the passage of plasma and plasma macromolecules but inhibits the passage of blood cells, and wherein the plasma transfer port has a plasma port cross-sectional geometry; and a plasma-receiving test substrate having a surface, said surface having thereon:
an absorptive element having a contact surface configured to engage the plasma transfer port and a plasma capacity which is less than a plasma capacity of the reservoir, and
at least one reaction zone disposed adjacent to the absorptive element, wherein plasma transferred from the reservoir will saturate the absorptive element to provide a measured amount of plasma which can be subsequently transferred to the reaction zone on the substrate.

18. A system as claimed in claim 17, wherein at least one reaction zone is separated from the absorptive element by a fluid-receiving surface, wherein fluid may be eluted from the absorptive element and flow onto the fluid-receiving surface and will be available to react within the reaction zone.

19. A system for transferring measured amounts of plasma from unmeasured blood samples to a test substrate, said system comprising:

an applicator having a blood-receiving reservoir with a predetermined plasma capacity and a single plasma transfer port having a cross-sectional area and shape in fluid communication with the reservoir and including a filter member extending across the plasma transfer port, wherein the filter member permits the passage of plasma and plasma macromolecules but inhibits the passage of blood cells; and a plasma-receiving test substrate having a surface, said surface having thereon:

a single absorptive element having a contact surface with a shape and area substantially identical to those of the port so that the contact surface is configured to engage the plasma transfer port and a plasma capacity which is less than the plasma capacity of the reservoir, wherein plasma transferred from the reservoir will saturate the absorptive element to provide a measured amount of plasma on the substrate;

a fluid-receiving surface disposed adjacent to the absorptive element, wherein fluid eluted from the absorptive element will flow onto the fluid-receiving surface; and at least one reaction zone separated from the absorptive element by the fluid-receiving surface, wherein fluid eluted from the absorptive element will be available to react with the reaction zone.

\* \* \* \* \*